US011723552B2

(12) United States Patent
Han et al.

(10) Patent No.: US 11,723,552 B2
(45) Date of Patent: Aug. 15, 2023

(54) FEEDING TUBE VISUALIZATION

(71) Applicant: UNM RAINFOREST INNOVATIONS, Albuquerque, NM (US)

(72) Inventors: Sang M. Han, Albuquerque, NM (US); Jarred Caldwell, Albuquerque, NM (US); Nicholas Brechtel, Albuquerque, NM (US); Nathan Madrid, Albuquerque, NM (US); Divya Prakash, Albuquerque, NM (US)

( * ) Notice: Subject to any disclaimer, the term of this patent is extended or adjusted under 35 U.S.C. 154(b) by 638 days.

(21) Appl. No.: 16/467,275

(22) PCT Filed: Dec. 7, 2017

(86) PCT No.: PCT/US2017/065159
§ 371 (c)(1),
(2) Date: Jun. 6, 2019

(87) PCT Pub. No.: WO2018/106947
PCT Pub. Date: Jun. 14, 2018

(65) Prior Publication Data
US 2019/0298222 A1    Oct. 3, 2019

Related U.S. Application Data

(60) Provisional application No. 62/431,883, filed on Dec. 9, 2016.

(51) Int. Cl.
*A61B 5/06* (2006.01)
*A61B 5/00* (2006.01)
*A61J 15/00* (2006.01)

(52) U.S. Cl.
CPC ............ *A61B 5/062* (2013.01); *A61B 5/0077* (2013.01); *A61B 5/4233* (2013.01);
(Continued)

(58) Field of Classification Search
CPC ....... A61B 5/061; A61B 5/062; A61B 5/0077; A61B 5/743; A61B 5/07; A61B 5/4233; A61B 5/4238; A61B 5/064; A61J 15/0003
See application file for complete search history.

(56) References Cited

U.S. PATENT DOCUMENTS 5,437,277 A * 8/1995 Dumoulin ................ A61B 5/06
                                                    600/424
5,553,618 A * 9/1996 Suzuki ....................... A61N 7/02
                                                    600/411
(Continued)

FOREIGN PATENT DOCUMENTS

WO         2007095541 A2     8/2007
WO      WO-2007095541 A2 *   8/2007  .......... A61J 15/0003
WO      WO-2016200334 A1 *  12/2016

OTHER PUBLICATIONS

Mathus-Vliegen et al., Nasoenteral feeding tube placement by nurses using an electromagnetic guidance system, Gasterointestinal endoscopy, vol. 71, No. 4 (2010); available at https://www.giejournal.org/article/S0016-5107(09)02700-X/pdf (Year: 2010).*

(Continued)

*Primary Examiner* — Christopher L Cook
*Assistant Examiner* — Mehdi Poursoltani
(74) *Attorney, Agent, or Firm* — MH2 Technology Law Group LLP

(57) ABSTRACT

An apparatus for determining a position of an object inside a body includes a first, detector configured to receive a signal from the object inside the body. The apparatus also includes a camera configured to capture an image or video of outside of a portion of the body, The object is positioned inside the portion of the body. A computing system is configured to receive the signal from the first detector and the image or video from the camera and to determine the (Continued)

position of the object Inside the body. A screen, is configured to display die position of the object inside the body.

21 Claims, 5 Drawing Sheets

(52) U.S. Cl.
CPC ............ *A61B 5/4238* (2013.01); *A61B 5/743* (2013.01); *A61J 15/0003* (2013.01)

(56) References Cited

U.S. PATENT DOCUMENTS

| | | | | |
|---|---|---|---|---|
| 5,782,765 | A * | 7/1998 | Jonkman | A61B 34/20 606/130 |
| 6,021,343 | A * | 2/2000 | Foley | A61B 17/16 600/417 |
| 6,211,666 | B1 * | 4/2001 | Acker | A61B 34/20 324/207.17 |
| 10,722,306 | B2 * | 7/2020 | Gliner | A61B 34/20 |
| 2002/0188194 | A1 * | 12/2002 | Cosman | A61B 90/16 378/205 |
| 2006/0004286 | A1 * | 1/2006 | Chang | A61B 90/16 606/198 |
| 2007/0078334 | A1 * | 4/2007 | Scully | A61B 5/06 600/424 |
| 2008/0228066 | A1 * | 9/2008 | Waitzman | A61J 15/0003 600/424 |
| 2009/0183740 | A1 * | 7/2009 | Sheffer | A61B 34/20 128/882 |
| 2009/0299175 | A1 * | 12/2009 | Bernstein | A61B 5/0507 600/425 |
| 2012/0041297 | A1 * | 2/2012 | McGary | A61N 5/1049 600/409 |
| 2012/0143049 | A1 * | 6/2012 | Neubauer | A61B 34/20 600/424 |
| 2013/0131503 | A1 * | 5/2013 | Schneider | G06T 7/97 600/424 |
| 2014/0107471 | A1 * | 4/2014 | Haider | A61B 17/1703 600/424 |
| 2014/0257081 | A1 * | 9/2014 | Rapoport | A61B 5/7455 600/409 |
| 2015/0031985 | A1 * | 1/2015 | Reddy | A61B 34/20 600/424 |
| 2015/0150440 | A1 * | 6/2015 | Salvati | A61B 1/00052 600/109 |
| 2016/0015292 | A1 * | 1/2016 | Lorraine | A61B 34/20 600/424 |
| 2016/0081583 | A1 * | 3/2016 | Ikuma | A61B 5/062 600/424 |
| 2016/0175064 | A1 * | 6/2016 | Steinle | A61B 90/39 600/424 |
| 2017/0119474 | A1 * | 5/2017 | Kronman | A61B 1/00006 |
| 2017/0347915 | A1 * | 12/2017 | Weprin | A61B 5/067 |

OTHER PUBLICATIONS

International Search Report and Written Opinion dated Mar. 15, 2018 in PCT Application No. PCT/US2017/065159, 6 pages.

* cited by examiner

FEEDING TUBE VISUALIZATION

CROSS-REFERENCE TO RELATED APPLICATIONS

This application is a U.S. National Phase application of PCT/US2017/065159 filed Dec. 7, 2017, which claims priority to U.S. Provisional Application having Ser. No. 62/431,883, filed Dec. 9, 2016, the entirety of which are incorporated herein by reference.

FIELD OF THE INVENTION

This invention relates generally to the field of detecting a location of an object inside a person, and more particularly to detecting and visualizing a location of a feeding tube inside a patient.

BACKGROUND OF THE INVENTION

Recovery of an ill patient in a hospital is often dependent on the enteral delivery of nutrients and medicine. For this reason, timely and accurate placement of a nasogastric feeding tube is important. The feeding tube is inserted through the nasal cavity and then manually positioned through the pylorus into the duodenum. Current insertion methods are time-consuming and involve frequent exposure to harmful ionizing radiation required to verify the position of the feeding tube. What is needed is an improved system and method for detecting and visualizing the location of an object (e.g., a feeding tube) inside a patient.

SUMMARY

An apparatus for determining a position of an object inside a body is disclosed. The apparatus includes a first, detector configured to receive a signal from the object inside the body. The apparatus also includes a camera configured to capture an image or video of an outside of a portion of the body. The object is positioned inside the portion of the body. A computing system is configured to receive the signal from the first detector and the image or video from the camera and to determine the position of the object inside the body. A screen is configured to display the position of the object inside the body.

In another embodiment, the apparatus includes a first metal detector, a second metal detector, and a third metal detector. The first metal detector, the second metal detector, and the third metal detector are each positional outside of the person and configured to transmit a first signal that is absorbed by a metallic lip of the feeding tube, which produces a second signal that is received by the respective first metal detector, second metal detector, and third metal detector. A camera is configured to capture an image or video of a contour determination device that is positioned over an abdomen of the person. The contour determination device includes a plurality of markers in a predetermined pattern. A computing system is configured to determine a position of the metallic tip of the feeding tube inside the abdomen of the person in response to the second signals received by the first metal detector, the second metal detector, and the third metal detector. The computing system is also configured to determine a size, location, and/or orientation of internal organs inside the abdomen of the person in response to the image or video of the plurality of markers on the contour determination device. A screen is configured to display the position of the metallic tip of the feeding tube with respect to the internal organs inside the abdomen of the person.

A method for determining a position of a feeding tube inside a body is also disclosed. The method includes introducing the feeding tube into the body. A first signal is transmitted with a first detector that is absorbed by a metallic tip of the feeding tube, which produces a second signal. The second signal is received with the first detector. A position of the metallic tip of the feeding tube inside the body is determined at least partially in response to the second signal. An image or video of a contour determination device that is positioned over an abdomen of the body is captured. The contour determination device includes a plurality of markers in a predetermined pattern. A size, location, and/or orientation of internal organs inside the body is determined in response to the image or video of the plurality of markers on the contour determination device. The position of the metallic tip of the feeding tube with respect to the internal organs inside the abdomen of the body is then displayed.

Advantages of the embodiments will be set forth in part in the description which follows, and in part will be understood from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass airy and nil sub-ranges subsumed (heroin. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the perimeter can take on negative values. In this case, the example value of range stated as "less than 10" can assume negative values, e.g., −1, −2, −3, −10, −20, −30, etc.

The following embodiments are described for illustrative purposes only with reference to the figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined will one or more other embodiments to form new embodiments.

Figure 1:
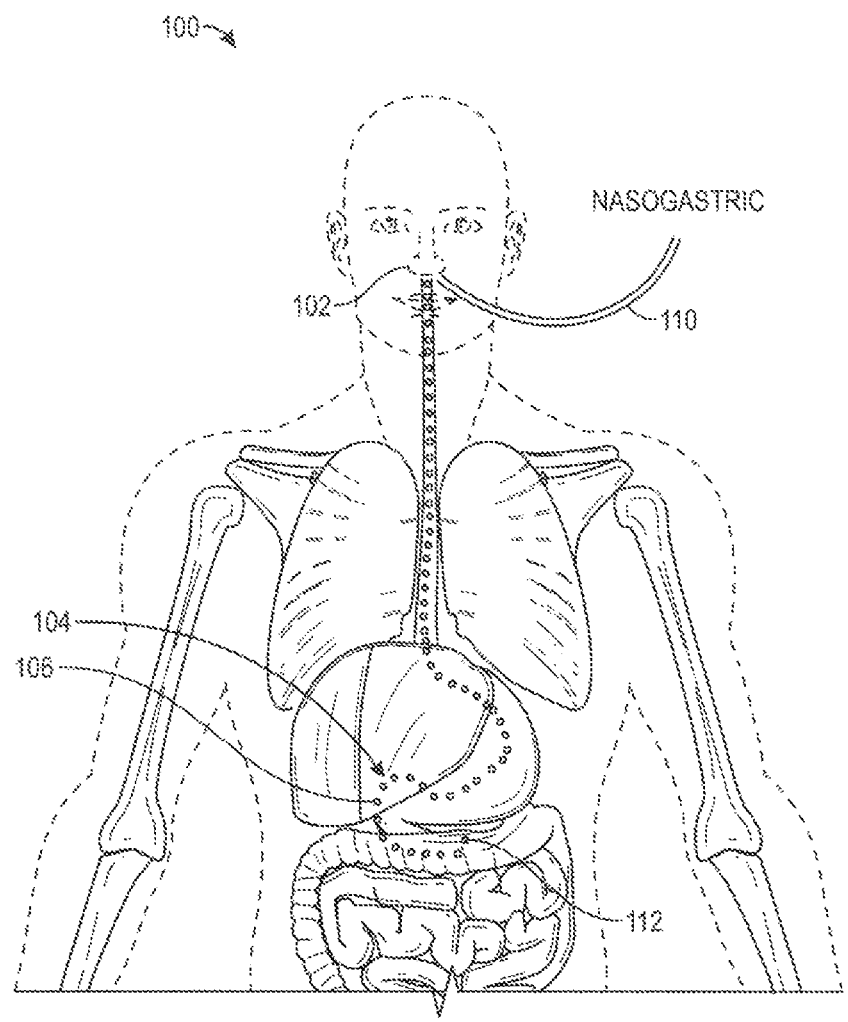
FIG. 1 illustrates a transparent view if a person having an object (e.g., a feeding tube) being introduced into the person through the natal cavity, according to an embodiment.

FIG. 1 illustrates a transparent view of a person 100 having an object 110 being introduced into the person 100, according to an embodiment. Although reference number 100 is used to identify a person herein, it will be appreciated that it may also or instead be used to identify an animal (e.g., a horse, a cow, a cat, a dog, etc.) or a non-living object. The object 110 may be or include a feeding tube. However, in other embodiments, the object 110 may be or include biomedical devices (e.g., endoscope, laparoscope, heart stents, etc.) as well as accidentally digested or inserted metal objects, including bullets, shrapnel, surgery tools, or the like.

The feeding tube 110 may be at least partially metallic. In one example, the feeding tube 110 may have a metallic distal tip 112, while the remainder of the feeding tube 110 may be made of biocompatible plastic. As shown, the metallic tip 112 of the feeding tube 110 may be introduced into the person (e.g., a patient) through the nasal cavity 102 and then manually positioned through the pylorus 104 into the duodenum 106. Once the metallic tip 112 is positioned in the duodenum 106, nutrients and or medicine may be pumped through the feeding tube 110 and into the duodenum 106.

Figure 2:
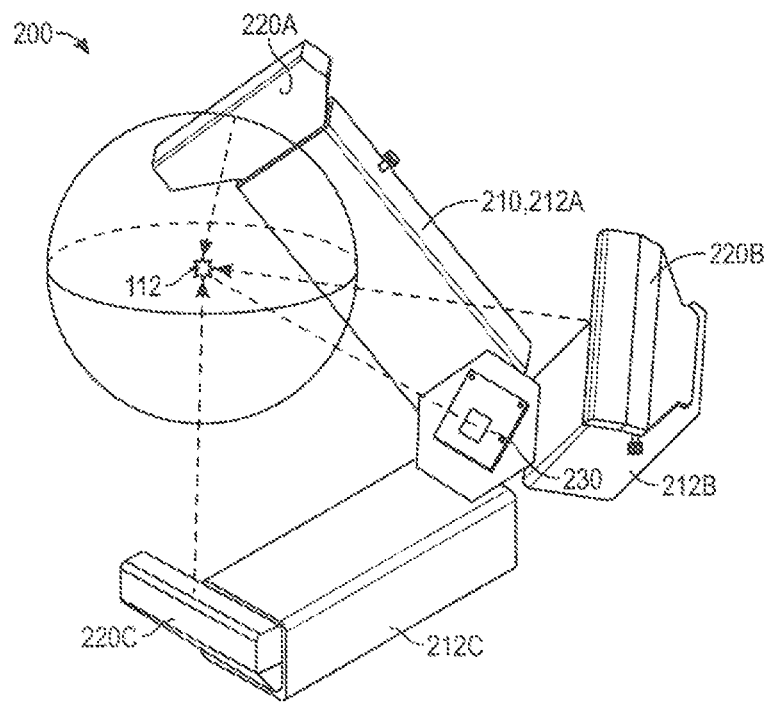
FIG. 2 illustrates a perspective view of an apparatus for detecting and visualizing a location of the object inside the person, according to an embodiment.
Figure 3:
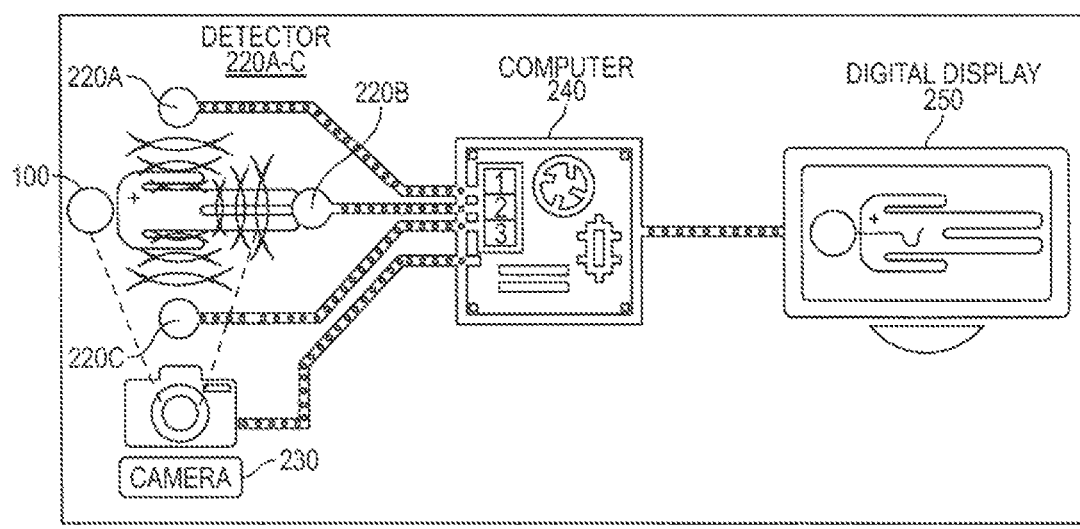
FIG. 3 illustrates a schematic view of the apparatus shown in FIG. 2, according to an embodiment.

FIGS. 2 and 3 illustrate a perspective view (FIG. 2) and a schematic view (FIG. 3) of an apparatus 200 for detecting and visualizing a location of the object (e.g., the feeding tube) 110 inside the person 100, according to an embodiment. More particularly, the apparatus 200 may be configured to be positioned outside the person 100 and to detect and visualize the location of the metallic tip 112 of the feeding tube 110 inside the person 100. The apparatus 200 may be cordless, portable, lightweight, and utilize sophisticated video-tracking software. The apparatus 200 may provide real-time 3D visualization of the feeding tube 110 with reference to the internal organs and tissues (e.g., esophagus, stomach, small intestines, etc.) in the patient's abdomen and may increase the success rate of positioning the feeding tube 110 to the post-pyloric region.

The apparatus 200 may include a body frame 210. The body frame 210 may include one or more arms (three are shown: 212A-C). The arms 212A-C may be substantially equidistant from each other. For example, the arms 212 A-C may be circumferentially-offset from one another (e.g., by 120°). The arms 212A-C may be in a fixed position, or the arms 212A-C may be configured to pivot to vary the distance between the distal ends of the arms 212A-C while the angle between the arms 212 A-C remains constant.

The apparatus 200 may also include one or more detectors (three are shown: 220A-C). The distal end of each arm 212A-C may have one of the detectors 220A-C coupled thereto. In one example, each detector 220A-C may be positioned in a sleeve and held in place by a pair of screws. The detectors 220A-C may be or include metal detectors (e.g., induction-based metal detectors) and/or magnetometers. Each detector 220A-C may be configured to transmit a first (e.g., electromagnetic) signal inward toward an area of signal overlap, which may be at least partially within the abdomen of the person 100. The first signal may be absorbed and/or reflected by the metallic tip 112 of the feeding tube 110 inside the person 100, which causes a second (e.g., electromagnetic) signal to be induced-generated in/by the metallic tip 112 that is detected/measured by the detectors 220A-C. In at least one embodiment, the first signals may be transmitted by the detectors 220A-C sequentially, as opposed to simultaneously, so as to not interfere with one another.

The strength of the second signals that are received by the detectors 220A-C may be proportional to the distance between the metallic tip 112 and the detectors 220A-C, allowing the distance between the metallic tip 112 and each detector 220A-C to be determined. When three detectors 220A-C are used, the precise position of the metallic tip 112 can be determined (e.g., triangulated) with respect to the apparatus 200.

In one embodiment, the detectors 220A-C may produce a very low frequency (VLF) first signal that is either continuous or discontinuous (e.g., a pulse induction signal). The detectors 220A-C may include one or more coils, and the coils may be mono-loop, double D, concentric, axial, or a combination thereof. The detection field for the coils may be conical, with the exception of the double D, which may be planar. In one example, the coils may be mono-loop, which may offer increased coverage (e.g., depth and area) for a particular size because one ring may be used for both transmission and detection. The mono-loop coil may be used in conjunction with the pulse induction signal. The pulse induction signal may also minimize opposing sensor field interactions when working on sample isolation in 3D.

The apparatus 200 may also include a camera 230. As shown, the camera 230 may be coupled to the body frame 210 (e.g., proximate to a centerpoint/apex of the arms 212A-C). The camera 230 may face inward toward the abdomen of the person 100.

The apparatus 200 may also include a computing system 240. As best shown in FIG. 3, the computing system 240 may be configured to receive the second signals from the detectors 220A-C, which may represent first input data. As mentioned above and discussed in greater detail below, the computing system 240 may process the first input data to triangulate the position of the metallic tip 112 inside the person 100 with respect to the apparatus 200.

The computing system 240 may also be configured to receive images and/or video from the camera 230, which may represent second input data. As discussed in greater detail below, the computing system 240 may process the second input data to measure/determine the outer contours of the abdomen of the person 100. From this, the computing system 240 may determine/estimate the size, location, and/or orientation of the menial organs (e.g., esophagus, stomach, small intestines, etc.) inside the abdomen of the person 100.

Thus, using the first and second inputs, the computing system 240 may determine the real-time position of the metallic tip 112 of the feeding tube 110 with respect to the internal organs inside the abdomen of the person 100. For example, the computing system 240 may be able to determine whether the metallic tip 112 is positioned within the duodenum 106.

The apparatus 200 may also include a graphical user interface (GUI) screen 250 or an augmented-reality eyewear. The screen 250 may be positioned on the back side of the body frame 210 (i.e., on the opposite side of the detector body frame 210 from the camera 230). Thus, while the camera 230 is pointed in toward the person (i.e., the patient) 100, a user of the apparatus 200 (e.g., a doctor or a nurse) may view the screen 250. The screen 250 may show, in 2D or 3D, the virtual internal organs of the person 100 and the real-time virtual location of the metallic tip 112 of the feeding tube 110 with reject to the internal organs of the person 100. In response to viewing this, the user (e.g., a doctor) may begin introducing nutrients and/or medicine into the feeding tube 110 if the metallic tip 112 is positioned in the desired location, or adjust the position of the feeding tube 110 inside the person 100 if the metallic tip 112 is not positioned in the desired location.

Figure 4:
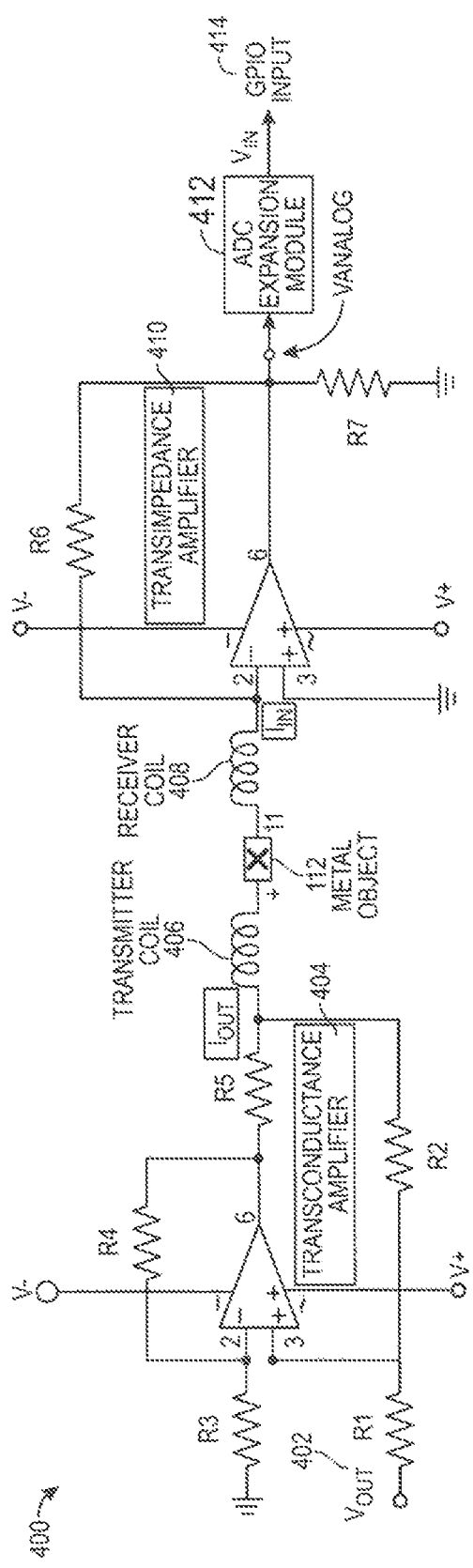
FIG. 4 illustrates a schematic view of a circuit for processing a signal transmitted by a (e.g., metal) detector of the apparatus to del ermine the location of the object inside the person, according to an embodiment.

FIG. 4 illustrates a schematic view of a circuit 400 for processing a signal transmitted by one of the detectors (e.g., detector 220A) or the apparatus 200, according to an embodiment. As shown, the circuit 400 may include a general-purpose input/output (GPIO) output 402 configured to generate an output voltage, a first (e.g., transconductance) amplifier 404, a transmitter coil 406 of the detector 220A, a receiver coil 408 of the detector 220A, a second (e.g., transimpedance) amplifier 410, an analog-to-digital (ADC) expansion module 412, and a GPIO input 414. The circuit 400 may also include a plurality of resistors (seven are shown: $R_1$, $R_2$, $R_3$, $R_4$, $R_5$, $R_6$, and $R_7$).

Figure 5:
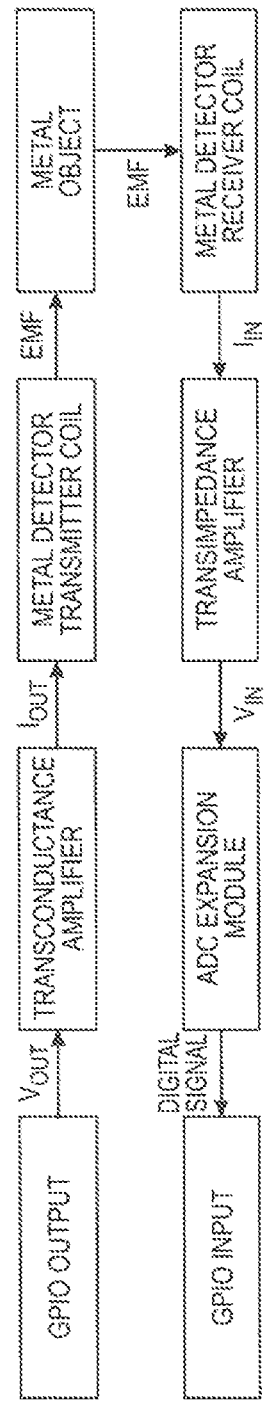
FIG. 5 illustrates a flowchart of the signal through the circuit, according to an embodiment.

FIG. 5 illustrates a flowchart 500 of the signal through the circuit 400, according to an embodiment. A voltage signal $V_{out}$ is output by the GPIO output 402. The voltage signal $V_{out}$ converted into a constant current level $I_{out}$ by the transconductance amplifier 404 and sent to the transmitter coil 406 of the detector 220A. This creates an electromagnetic field (EMF), which is absorbed by the metallic tip 112 of the feeding tube 110. The metallic tip 112 subsequently creates an induced secondary EMF, which is received by the receiver coil 408 of the detector 220A. This induces an electrical current $I_{in}$ in the receiver coil 408 having an amplitude that is proportional to its proximity (e.g., distance) to the metallic tip 112. This current $I_{in}$ is converted into an analog voltage signal by the transimpedance amplifier 410. The ADC expansion module 412 converts, the analog voltage signal $V_{analog}$ into a digital signal $V_{in}$ 414 that is readable by a GPIO input of the computing system 240. The digital signals from the detectors 220A-C may be considered to be a first input (or a plurality of first inputs) into the computing system 240.

The voltage $V_{out}$ may be convened to current $I_{out}$ in the transconductance amplifier 504 by the following relationships:

$$I_{out} = \frac{V_{out} \cdot R_2}{R_5 \cdot R_1} \tag{1}$$

$$\frac{R_2}{R_1} = \frac{R_4}{R_3} \tag{2}$$

The current may be converted back to voltage in the transimpedance amplifier 310 by the following relationship:

$$V_{analog} = -\frac{I_{in}}{R_6} \tag{3}$$

This input analog voltage signal $V_{analog}$ is then sent to the ADC expansion module 412.

Figure 6:
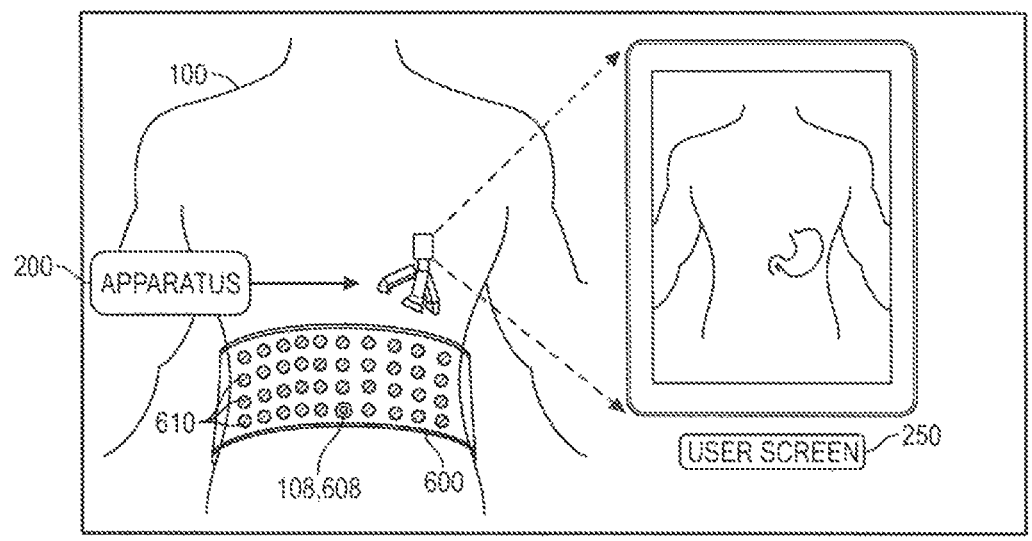
FIG. 6 illustrates a contour determination device that is to be positioned on the person and viewed by a camera of the apparatus, according to an embodiment.

FIG. 6 illustrates a contour determination device 600 that is positioned on the (e.g., abdomen of the) person 100, according loan embodiment. The contour determination device 600 may be or include a cloth, a belt, a shin, or the like that is positioned on the abdomen of the person 100 and is substantially skin-tight over the outer contours of the abdomen, The contour determine device 600 may be positioned at a particular ideation 108 with respect to the person 100. For example, a point 608 on the contour determine device 600 may be aligned with the particular location (e.g., the navel) 108 of the person 100.

The contour determination device 600 may include a predetermined pattern on an exterior fabric thereof that may be viewed by the camera 230. As shown, the predetermined pattern may be or include a series of markers (e.g., circles or dots) 610 that are arranged in rows and columns with a predetermined spacing between the markers 610. However, as will be appreciated, the markers 610 may be or include any set of snipes (e.g., triangles, rectangles, stars, etc.) that is arranged with a constant spacing or a random spacing.

Figures 7A, 7B, 7C:
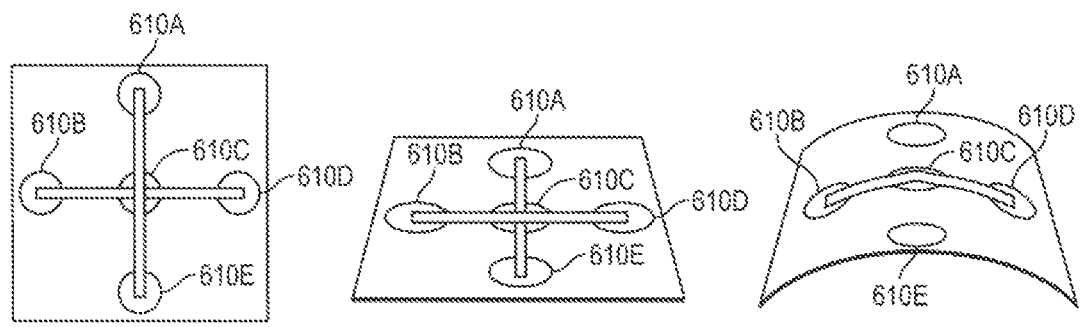
FIGS. 7A-C illustrate a planar view (FIG. 7A), an angled view (FIG. 7B), and a curved view (FIG. 7C) of markers on the contour determination device, according to an embodiment.

FIGS. 7A-C illustrate a planar view (FIG. 7A), an angled birds-eye view (FIG. 7B), and a curved view (FIG. 7C) of five of the markers 610A-E on the contour determination device 600, according to an embodiment. As will be appreciated, the size, shape, positioning, orientation, and/or color rendition of the markers 610A-C viewed on a display may vary, depending, upon the size and shape of the abdomen of the person 100. The camera 230 may capture images and/or video of the markers 610A-E, and the computing system 240 may determine the contours of the abdomen of the person 100 by measuring and determining: (1) the distance between the apparatus 200 (e.g., the camera 230) and each marker 610A-E, (2) the distance between each adjacent pair of markers (e.g., markers 610B and 610C), (3) apparent length across each marker 610A-C in one or more directions, which may be indicative of the angle and/or curve of the markers 610A-C, or a combination thereof. Then, as discussed above, once the contours of the abdomen are determined, the computing system 240 may use this information to estimate/determine the size, location, and/or orientation of the internal organs (e.g., esophagus, stomach, small intestines, etc.) inside the abdomen of the person 100.

Figure 8:
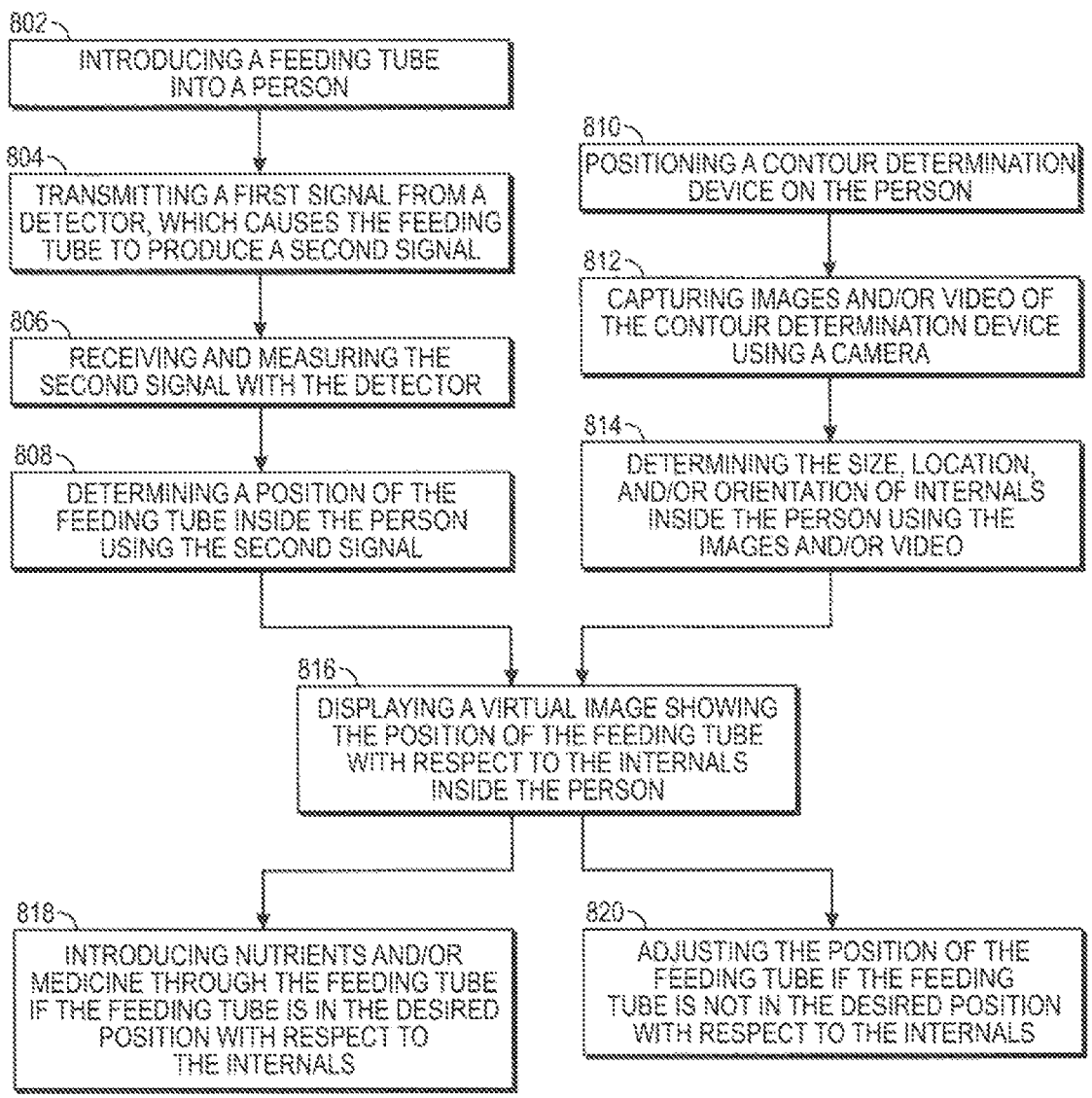
FIG. 8 illustrates a flowchart of a method for positioning the object in a desired location in the person, according to an embodiment.

FIG. 8 illustrates a flowchart of a method 800 for positioning the (metallic tip 112 of the) feeding tube 110 in a desired location in the person 100, according to an embodiment. The method HOC may include introducing the feeding tube 110 into the person 100, as of 802. For trample, the feeding tube 110 may be introduced into the person 100 through the nasal cavity 102. The method 800 may also include transmitting one or more first signals from the detectors 220A-C, as at 804. As discussed above, the first signals may be absorbed/reflected by the metallic tip 112 of the feeding tube 110, which causes one or more second signals to be induced generated in/by the metallic tip 112. The method 800 may also include receiving and measuring the one or more second signals using the detectors 220A-C, as at 806. As mentioned above, the second signals may be the first input into the computing system 240 of the apparatus 200. The method 800 may also include determining (e.g., triangulating) the position of the metallic tip 112 in response in the second signals using the computing system 240, as at 808.

The method 800 may also include petitioning the contour determination device 600 on the (e.g., abdomen of the) person 100, as at 810. The method 800 may also include capturing images and/or video of the (e.g., markers 610 on the) contour determination device 600 using the camera 230, as at 812. As mentioned above, the images and/or video may be the second input into the computing system 240 of the apparatus 200. The method 800 may also include determining/estimating the (e.g., size, location, and/or orientation of the) internal organs inside the abdomen of the person 100 using the computing system 240, as at 814. The steps 804-808 may occur before, simultaneously with, or after the steps 810-814.

The method 800 may also include displaying a virtual image on the screen 250 of the apparatus 200 showing the real-time position of the metallic tip 112 of the feeding tube 110 with respect to the internal organs inside the abdomen of the person 100, as at 816. The method 800 may also include introducing (e.g. pumping) nutrients and/or medicine through the feeding tube 110 if the metallic tip 112 is in the desired position (e.g., the duodenum 106) in the person 100, as at 818. Alternatively, if the metallic tip 112 is not in the desired position, the method 800 may include adjusting the position of the feeding tube 110 inside the person 100 until the metallic tip 112 is in the desired position, as at 820.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function.

Furthermore, to the extent that the terms "including", "includes", "having", "has", "with", or variants thereof are used in either the detailed description and the claims, such terms are intended to be inclusive in a manner similar to the term "comprising." As used herein, the phrase "one or more of", for example, A, B, and C means any of the following: either A, B, or C alone, or combinations of two, such as A and B, B and C, and A and C; or combinations of three A, B and C.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for determining a position of an object inside a body, comprising:
a frame comprising:
a first arm;
a second arm; and
a third arm;
a first detector coupled to an outer end of the first arm;
a second detector coupled to an outer end of the second arm;
a third detector coupled to an outer end of the third arm, wherein the first, second, and third detectors each comprise a transmitter coil and a receiver coil, wherein the transmitter coil is configured to generate a first wireless signal that is absorbed by a metallic tip of the object in the body, wherein the metallic tip generates a second wireless signal in response to absorbing the first wireless signal, and wherein the receiver coil is configured to receive the second wireless signal;
a plurality of circuits including at least a first circuit connected to the first detector, a second circuit connected to the second detector, and a third circuit connected to the third detector, wherein each circuit is configured to process the second wireless signal from the respective detector, and wherein each circuit comprises:
an output configured to generate an output voltage;
a transconductance amplifier connected to the output and the transmitter coil of the respective detector, wherein the transconductance amplifier is configured to convert the output voltage to a constant first current, and wherein the transmitter coil of the respective detector generates the first wireless signal in response to the constant first current;
a transimpedance amplifier connected to the receiver coil of the respective detector, wherein the second wireless signal received by the receiver coil of the respective detector induces a second current that is converted into an analog voltage by the transimpedance amplifier;
an analog-to-digital expansion module connected to the transimpedance amplifier, wherein the analog-to-digital expansion module is configured to convert the analog voltage into a digital voltage; and
an input connected to the analog-to-digital expansion module and configured to receive the digital voltage;
a camera coupled to the frame proximate to inner ends of the first, second, and third arms, wherein the camera is configured to capture an image or video of an outside of a portion of the body, wherein the object is positioned inside the portion of the body;
a computing system configured to receive the digital voltage from the input, and the image or video from the camera, and to determine the position of the object inside the body based at least partially upon the digital voltage and the image or video; and
a screen coupled to the frame proximate to the inner ends of the first, second, and third arms, wherein the screen is on an opposite side of the frame from the camera, and wherein the screen is configured to display the position of the object inside the body.

2. The apparatus of claim 1, wherein the object comprises a feeding tube having a metallic tip.

3. The apparatus of claim 1, wherein the camera is configured to capture the image or video of a contour determination device that is positioned on the outside of the portion of the body, and wherein the portion comprises an abdomen.

4. The apparatus of claim 3, wherein the contour determination device is positioned over the outside of the abdomen of the body, and wherein the contour determination device comprises a plurality of markers in a predetermined pattern.

5. The apparatus of claim 4, wherein the computing system is also configured to determine a size, location, and/or orientation of internal organs inside the abdomen of the body in response to the image or video of the plurality of markers on the contour determination device.

6. The apparatus of claim 5, wherein the screen is configured to display the position of the object inside the body with respect to the internal organs inside the abdomen of the body.

7. The apparatus of claim 1, wherein an amplitude of the second wireless signals received by the first detector, the second detector, and the third detector is proportional to a distance between the object and the first detector, the second detector, and the third detector, respectively, enabling the computing system to triangulate the position of the object inside the body with respect to the apparatus.

8. An apparatus for determining a position of a feeding tube inside a person, comprising:
   a frame comprising a first arm, a second arm, and a third arm, wherein the first, second, and third arms are circumferentially offset from one another with respect to an axis through the frame;
   a first metal detector coupled to an outer end of the first arm;
   a second metal detector coupled to an outer end of the second arm;
   a third metal detector coupled to an outer end of the third arm, wherein the first metal detector, the second metal detector, and the third metal detector are each positioned outside of the person and each comprise a transmitter coil and a receiver coil, wherein the transmitter coil is configured to transmit a respective first signal that is absorbed by a metallic tip of the feeding tube, which produces a respective second signal that is received by the receiver coil;
   a plurality of circuits including at least a first circuit connected to the first metal detector, a second circuit connected to the second metal detector, and a third circuit connected to the third metal detector, wherein each circuit is configured to process the second signal from the respective metal detector, wherein each circuit comprises:
      an output configured to generate an output voltage;
      a transconductance amplifier connected to the output and the transmitter coil of the respective metal detector, wherein the transconductance amplifier is configured to convert the output voltage to a constant first current, and wherein the transmitter coil of the respective metal detector generates the respective first signal in response to the constant first current;
      a transimpedance amplifier connected to the receiver coil of the respective metal detector, wherein the respective second signal received by the receiver coil of the respective metal detector induces a second current that is converted into an analog voltage by the transimpedance amplifier; and
      an analog-to-digital expansion module connected to the transimpedance amplifier, wherein the analog-to-digital expansion module is configured to convert the analog voltage into a digital voltage;
   a camera coupled to the frame proximate to inner ends of the first, second, and third arms, wherein the camera faces toward the body, wherein the camera is configured to capture an image or video of a contour determination device that is positioned over an abdomen of the person, and wherein the contour determination device comprises a plurality of markers in a predetermined pattern;
   a computing system configured to:
      determine a position of the metallic tip of the feeding tube inside the abdomen of the person in response to the digital voltage; and
      determine a size, location, and/or orientation of internal organs inside the abdomen of the person in response to the image or video of the plurality of markers on the contour determination device; and
   a screen coupled to the frame proximate to the inner ends of the first, second, and third arms, wherein the screen faces away from the body, and wherein the screen is configured to display the position of the metallic tip of the feeding tube with respect to the internal organs inside the abdomen of the person to aid a user in navigating the feeding tube around the internal organs and into a duodenum in the body.

9. The apparatus of claim 8, wherein the camera and the screen are coupled to the frame proximate to an intersection of the three arms.

10. The apparatus of claim 8, wherein the respective first signals are transmitted sequentially by the first metal detector, the second metal detector, and the third metal detector so as to not interfere with one another.

11. The apparatus of claim 8, wherein the first metal detector comprises a mono-loop coil, and wherein the first signal transmitted by the first metal detector comprises a pulse induction signal.

12. The apparatus of claim 8, wherein the computing system is configured to determine one or more outer contours of the abdomen in response to the image or video of the plurality of markers on the contour determination device, and wherein the computing system is configured to determine the size, location, and/or orientation of internal organs inside the abdomen in response to the one or more outer contours of the abdomen.

13. A method for determining a position of a feeding tube inside a body, comprising:
   positioning an apparatus with respect to the body, wherein the apparatus comprises a frame having a first arm with a first detector at an outer end thereof, a second arm with a second detector at an outer end thereof, and a third arm with a third detector at an outer end thereof, and wherein the apparatus is positioned such that the body is between and spaced apart from the first, second, and third detectors;
   introducing the feeding tube into the body;
   generating respective output voltages;
   converting the respective output voltages to respective constant first currents;
   generating respective first signals with transmitter coils in the first, second, and third detectors in response to the respective constant first currents, wherein the respective first signals are absorbed by a metallic tip of the feeding tube, which generates respective second signals;
   receiving the respective second signals with receiver coils in the first, second, and third detectors, wherein the second respective signals induce respective second currents;
   converting the respective second currents into respective analog voltages;
   converting the respective analog voltages into respective digital voltages;

determining a position of the metallic tip of the feeding tube inside the body at least partially in response to the respective digital voltages;

capturing an image or video of a contour determination device that is positioned over an abdomen of the body using a camera that is coupled to the frame proximate to inner ends of the first, second, and third arms, wherein the contour determination device comprises a plurality of markers in a predetermined pattern;

determining a size, location, and/or orientation of internal organs inside the body in response to the image or video of the plurality of markers on the contour determination device; and displaying, on a screen, the position of the metallic tip of the feeding tube with respect to the internal organs inside the abdomen of the body, wherein the screen is coupled to the frame proximate to inner ends of the first, second, and third arms, and wherein the screen is on an opposite side of the frame from the camera.

14. The method of claim 13, further comprising introducing nutrients or medicine into the feeding tube when the metallic tip of the feeding tube is positioned within a duodenum of the body.

15. The method of claim 13, further comprising adjusting a position of the feeding tube inside the body when the metallic tip of the feeding tube is not positioned within a duodenum of the body.

16. The method of claim 13, wherein the first, second, and third detectors are spaced equidistant from one another around an axis through the frame.

17. The method of claim 16, wherein the first, second, and third detectors are configured to transmit the respective first signals sequentially.

18. The apparatus of claim 8, wherein the first, second, and third arms are configured to pivot to vary distances between the first, second, and third arms while angles between the first, second, and third arms remain constant.

19. The apparatus of claim 1, wherein the circuit further comprises:
a first resistor connected to a positive input terminal of the first transconductance amplifier;
a second resistor connected to the first resistor and to the transmitter coil;
a third resistor connected to a negative input terminal of the first transconductance amplifier;
a fourth resistor connected to the third resistor and to an output terminal of the first transconductance amplifier; and
a fifth resistor having an upstream end connected to the fourth resistor and a downstream end connected to the second resistor and the transmitter coil.

20. The apparatus of claim 19, wherein the output voltage is converted into the constant first current based upon the following equations:

$$I_{out} = \frac{V_{out} \cdot R_2}{R_5 \cdot R_1} \quad (1)$$

$$\frac{R_2}{R_1} = \frac{R_4}{R_3} \quad (2)$$

where $I_{out}$ represents the constant first current, $V_{out}$ represents the output voltage, $R_1$ represents a resistance of the first resistor, $R_2$ represents a resistance of the second resistor, $R_3$ represents a resistance of the third resistor, $R_4$ represents a resistance of the fourth resistor, and $R_5$ represents a resistance of the fifth resistor.

21. The apparatus of claim 20, wherein the circuit further comprises a sixth resistor connected to the receiver coil, a negative input terminal of the transimpedance amplifier and an output terminal of the transimpedance amplifier, and wherein the second current is converted into the analog voltage by the following equation:

$$V_{analog} = -\frac{I_{in}}{R_6} \quad (3)$$

where $V_{analog}$ represents the analog voltage, $I_{in}$ represents the second current, and $R_6$ represents a resistance of the sixth resistor.

* * * * *

UNITED STATES PATENT AND TRADEMARK OFFICE
CERTIFICATE OF CORRECTION

PATENT NO. : 11,723,552 B2
APPLICATION NO. : 16/467275
DATED : August 15, 2023
INVENTOR(S) : Sang M. Han et al.

Page 1 of 1

It is certified that error appears in the above-identified patent and that said Letters Patent is hereby corrected as shown below:

On the Title Page

Item (57) Under Abstract, Line 2, "first, detector" should be --first detector--.

Item (57) Under Abstract, Line 5, "of outside" should be --of an outside--.

Item (57) Under Abstract, Line 5, "body, The" should be --body. The--.

On page (2)

Item (57) Under Abstract, Line 9, "Inside" should be --inside--.

Item (57) Under Abstract, Line 9, "screen, is" should be --screen is--.

Item (57) Under Abstract, Line 10, "die" should be --the--.

Signed and Sealed this
Tenth Day of October, 2023

Katherine Kelly Vidal
*Director of the United States Patent and Trademark Office*